US008785709B2

(12) United States Patent
Ratnasamy et al.

(10) Patent No.: US 8,785,709 B2
(45) Date of Patent: Jul. 22, 2014

(54) CATALYTIC ISOMERISATION OF LINEAR OLEFINIC HYDROCARBONS

(75) Inventors: Paul Ratnasamy, Pune (IN); Moises Carreon, Louisville, KY (US); Chinmay Deshmane, Winston Salem, NC (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 219 days.

(21) Appl. No.: 13/436,129

(22) Filed: Mar. 30, 2012

(65) Prior Publication Data

US 2012/0253087 A1 Oct. 4, 2012

Related U.S. Application Data

(60) Provisional application No. 61/469,384, filed on Mar. 30, 2011.

(51) Int. Cl.
| | |
|---|---|
| *C07C 5/27* | (2006.01) |
| *C07C 5/22* | (2006.01) |
| *B01J 23/20* | (2006.01) |
| *B01J 35/00* | (2006.01) |
| *B01J 35/10* | (2006.01) |
| *B01J 37/10* | (2006.01) |
| *B01J 35/08* | (2006.01) |
| *B01J 37/00* | (2006.01) |

(52) U.S. Cl.
CPC ............ *C07C 5/2772* (2013.01); *B01J 23/20* (2013.01); *B01J 35/002* (2013.01); *B01J 35/006* (2013.01); *B01J 35/1019* (2013.01); *B01J 3/036* (2013.01); *C07C 2523/20* (2013.01); *B01J 37/10* (2013.01); *C07C 2523/08* (2013.01); *B01J 35/08* (2013.01); *B01J 35/1061* (2013.01); *B01J 37/0018* (2013.01)
USPC .......................................... 585/671; 585/500

(58) Field of Classification Search
CPC ...... C07C 5/2735; C07C 5/2705; C07C 11/02
USPC .......................................... 585/16, 240, 671
See application file for complete search history.

(56) References Cited

U.S. PATENT DOCUMENTS

| | | | |
|---|---|---|---|
| 2,156,863 A | 5/1939 | Mills | |
| 3,530,198 A | 9/1970 | Fenton | |
| 3,620,961 A | 11/1971 | Ireland | |
| 3,948,761 A * | 4/1976 | Siskin et al. ................ | 585/743 |
| 3,984,444 A | 10/1976 | Ritz | |
| 4,038,172 A | 7/1977 | Ueda et al. | |
| 4,385,994 A | 5/1983 | Wilson | |
| 4,554,397 A | 11/1985 | Stern | |
| 4,689,138 A | 8/1987 | Miller | |
| 5,053,373 A | 10/1991 | Zones | |
| 5,252,527 A | 10/1993 | Zones | |
| 5,282,958 A * | 2/1994 | Santilli et al. ............ | 208/111.15 |
| 5,397,454 A | 3/1995 | Zones | |
| 5,406,018 A * | 4/1995 | Sherman ........................ | 585/729 |
| 5,510,309 A | 4/1996 | Chang | |
| 5,525,126 A | 6/1996 | Basu | |
| 5,705,722 A | 1/1998 | Monnier et al. | |
| 5,780,382 A | 7/1998 | Chang | |
| 5,854,170 A | 12/1998 | Chang | |
| 5,856,539 A | 1/1999 | Hodgson | |
| 5,908,946 A | 6/1999 | Stern | |
| 6,015,440 A | 1/2000 | Noureddini | |
| 6,060,633 A * | 5/2000 | Chen et al. ................... | 585/475 |
| 6,124,232 A | 9/2000 | Chang | |
| 6,147,196 A | 11/2000 | Stern | |
| 6,255,504 B1 | 7/2001 | Roberts | |
| 6,455,716 B2 | 9/2002 | Kenneally | |
| 6,489,496 B2 | 12/2002 | Barnhorst | |
| 6,638,891 B2 * | 10/2003 | Karim et al. .................. | 502/302 |
| 6,818,589 B1 | 11/2004 | Gillespie | |
| 6,831,184 B2 | 12/2004 | Zhang | |
| 6,878,837 B2 | 4/2005 | Bournay | |
| 6,946,567 B2 * | 9/2005 | Zhang et al. .................. | 554/125 |
| 6,960,672 B2 | 11/2005 | Nakayama | |
| 6,992,057 B2 | 1/2006 | Connor | |
| 7,122,688 B2 | 10/2006 | Lin | |
| 7,141,529 B2 | 11/2006 | Biscardi | |
| 7,232,935 B2 | 6/2007 | Jakkula et al. | |
| 7,368,626 B2 * | 5/2008 | Matsushita ................... | 585/750 |
| 7,491,858 B2 | 2/2009 | Murzin et al. | |
| 7,511,181 B2 | 3/2009 | Petri et al. | |
| 7,754,643 B2 | 7/2010 | Srinivas | |
| 7,803,269 B2 | 9/2010 | Kokayeff et al. | |

(Continued)

FOREIGN PATENT DOCUMENTS

| | | |
|---|---|---|
| EP | 2141217 A1 | 1/2010 |
| EP | 2097496 B1 | 12/2010 |

(Continued)

OTHER PUBLICATIONS

Banerjee et al., "High-Throughput Synthesis of Zeolitic Imidazolate Frameworks and Applications in CO2 Capture," Science, vol. 319, pp. 939-943, 2008.

(Continued)

*Primary Examiner* — Ellen McAvoy

(74) *Attorney, Agent, or Firm* — Wyatt, Tarrant & Combs, LLP; Stephen C. Hall

(57) ABSTRACT

Gallium-niobium oxide catalysts are disclosed herein for converting linear olefinic hydrocarbons to branched olefinic hydrocarbons through isomerization, the latter being capable for use fuel for their desirable properties.

8 Claims, No Drawings

(56) References Cited

U.S. PATENT DOCUMENTS

| | | | |
|---|---|---|---|
| 7,816,570 B2 | 10/2010 | Roberts | |
| 7,880,043 B2 | 2/2011 | Chapus et al. | |
| 7,888,542 B2 | 2/2011 | Koivusalmi et al. | |
| 7,897,824 B2 | 3/2011 | Aulich et al. | |
| 7,915,460 B2 | 3/2011 | Kalnes et al. | |
| 7,928,273 B2 | 4/2011 | Bradin et al. | |
| 7,960,597 B2 | 6/2011 | Miller | |
| 7,968,757 B2 | 6/2011 | Abhari et al. | |
| 7,982,075 B2 | 7/2011 | Marker et al. | |
| 7,982,076 B2 | 7/2011 | Marker et al. | |
| 7,989,671 B2 | 8/2011 | Strege et al. | |
| 7,999,142 B2 | 8/2011 | Kalnes et al. | |
| 8,003,836 B2 | 8/2011 | Marker et al. | |
| 8,022,258 B2 | 9/2011 | Myllyoja et al. | |
| 8,026,401 B2 | 9/2011 | Abhari et al. | |
| 8,039,682 B2 | 10/2011 | McCall et al. | |
| 8,058,492 B2 | 11/2011 | Anumakonda et al. | |
| 8,067,653 B2 | 11/2011 | Bressler | |
| 8,084,655 B2 | 12/2011 | Dindi et al. | |
| 8,119,847 B2 | 2/2012 | Dindi et al. | |
| 8,193,400 B2 | 6/2012 | Brady et al. | |
| 8,197,559 B2 | 6/2012 | Abe et al. | |
| 8,212,094 B2 | 7/2012 | Myllyoja et al. | |
| 8,247,632 B2 | 8/2012 | Strege et al. | |
| 8,592,638 B2 * | 11/2013 | Aalto et al. | 585/240 |
| 2002/0045787 A1 | 4/2002 | Le Peltier et al. | |
| 2003/0191330 A1 | 10/2003 | Zhang et al. | |
| 2007/0010682 A1 | 1/2007 | Myllyoja et al. | |
| 2007/0135316 A1 | 6/2007 | Koivusalmi et al. | |
| 2008/0052983 A1 | 3/2008 | Aulich et al. | |
| 2008/0229654 A1 | 9/2008 | Bradin | |
| 2008/0244962 A1 | 10/2008 | Abhari | |
| 2008/0302001 A1 | 12/2008 | Koivusalmi | |
| 2009/0047721 A1 | 2/2009 | Trimbur et al. | |
| 2009/0069610 A1 | 3/2009 | Roberts | |
| 2009/0318737 A1 | 12/2009 | Luebke | |
| 2009/0326252 A1 | 12/2009 | Srinivas | |
| 2010/0036183 A1 | 2/2010 | Gudde et al. | |
| 2010/0056839 A1 | 3/2010 | Ramachandran et al. | |
| 2010/0069690 A1 | 3/2010 | Gudde | |
| 2010/0076236 A1 | 3/2010 | Van Heuzen et al. | |
| 2010/0160698 A1 | 6/2010 | Perego et al. | |
| 2010/0228068 A1 | 9/2010 | O'Connor et al. | |
| 2011/0005190 A1 | 1/2011 | Bauldreay et al. | |
| 2011/0039102 A1 | 2/2011 | Chaumonnot et al. | |
| 2011/0105813 A1 | 5/2011 | Roberts, IV et al. | |
| 2011/0105817 A1 | 5/2011 | Zwijnenburg et al. | |
| 2011/0131867 A1 | 6/2011 | Kalnes et al. | |
| 2011/0166405 A1 | 7/2011 | Van Beijnum et al. | |
| 2011/0196197 A1 | 8/2011 | Forsell | |
| 2012/0083633 A1 | 4/2012 | Aulich et al. | |
| 2012/0108861 A1 | 5/2012 | Roberts, IV et al. | |
| 2012/0136185 A1 | 5/2012 | Bressler | |
| 2012/0151825 A1 | 6/2012 | Leonard | |
| 2012/0157734 A1 | 6/2012 | Strege et al. | |
| 2012/0203040 A1 | 8/2012 | Ratnasamy | |
| 2013/0252804 A1 * | 9/2013 | Ramachandran et al. | 502/176 |

FOREIGN PATENT DOCUMENTS

| | | |
|---|---|---|
| FI | 100248 | 10/1997 |
| FI | EP1681337 | 7/2006 |
| GB | 335543 A | 9/1930 |
| GB | 3355543 A | 9/1930 |
| WO | 2007027955 A2 | 3/2007 |
| WO | 2007027955 A3 | 5/2007 |
| WO | 2007068791 A1 | 6/2007 |
| WO | 2007068800 A2 | 8/2007 |
| WO | 2007068800 A3 | 8/2007 |
| WO | 2008029301 A2 | 3/2008 |
| WO | 2008040980 A1 | 4/2008 |
| WO | 2008058664 A1 | 5/2008 |
| WO | 2008081101 A2 | 7/2008 |
| WO | 2008101945 A1 | 8/2008 |
| WO | 2008103204 A2 | 8/2008 |
| WO | 2008081101 A3 | 11/2008 |
| WO | 2008157465 A2 | 12/2008 |
| WO | 2009008893 A1 | 1/2009 |
| WO | 2009038965 A1 | 3/2009 |
| WO | 2009039000 A2 | 3/2009 |
| WO | 2009039347 A1 | 3/2009 |
| WO | 2009039000 A3 | 6/2009 |
| WO | 2009085686 A1 | 7/2009 |
| WO | 2009095711 A1 | 8/2009 |
| WO | 2008103204 A3 | 9/2009 |
| WO | 2009117426 A1 | 9/2009 |
| WO | 2008157465 A3 | 11/2009 |
| WO | 2009117426 A1 | 12/2009 |
| WO | 2010000934 A1 | 1/2010 |
| WO | 2010008686 A2 | 1/2010 |
| WO | 2010022254 A2 | 2/2010 |
| WO | 2009151692 A3 | 4/2010 |
| WO | 2010008686 A3 | 4/2010 |
| WO | 2010043765 A1 | 4/2010 |
| WO | 2010053896 A2 | 5/2010 |
| WO | 2010022254 A3 | 6/2010 |
| WO | 2010068203 A1 | 6/2010 |
| WO | 2010053896 A3 | 7/2010 |
| WO | 2008029301 A3 | 3/2011 |
| WO | 2011073427 A1 | 6/2011 |
| WO | 2011073431 A2 | 6/2011 |
| WO | 2011073431 A3 | 8/2011 |
| WO | 2012091905 A1 | 7/2012 |
| WO | 2012106637 A1 | 8/2012 |

OTHER PUBLICATIONS

Banerjee et al., "Control of Pore Size and Functionality in Isoreticular Zeolitic Imidazolate Frameworks and Their Carbon Dioxide Selective Capture Properties," J. Am. Chem. Soc., 131, pp. 3875-3877, 2009.

Christy, "Evidence of the formation of conjugated linoleic acids from thermally induced 9t12t linoleic acid: a study by gas chromotography and infrared spectroscopy," Chemistry and Physics in Lipids, vol. 161, pp. 86-94, 2009.

Cravillon et al., "Rapid Room-Temperature Synthesis and Characterization of Nanocrystals of a Prototypical Zeolitic Imidazolate Framework," Chem. Material, vol. 21, pp. 1410-1412, 2009.

Danuthai et al., "Conversion of methylesters to hydrocarbons over an H-ZSM5 zeolite catalyst," Applied Catalysis A: General 361, pp. 99-105, 2009.

Deshmane et al., "Thermally Stable Nanocrystalline Mesoporous Gallium Oxide Phases," Eur. J. Inor. Chem., vol. 22, pp. 3275-3281, 2009.

Dunn et al., "Improving the Low-Temperature Properties of Alternative Diesel Fuels: Vegetable Oil-Derived Methyl Esters," J. Am. Oil Chem. Soc., vol. 73, No. 12, pp. 1719-1728, 1996.

Gryglewicz, "Rapeseed oil methyl esters preparation using heterogeneous catalysts," Bioresource Technology, vol. 70, pp. 249-253, 1999.

Hayashi et al., "Zeolite a imidazolate frameworks," Nature Materials, vol. 6, pp. 501-506, 1999.

Huang et al., "Ligand-Directed Strategy for Zeolite-Type Metal-Organic Frameworks: Zinc(ii) Imidazolates with Unusual Zeolitic Topologies," Angewandte Chemie International Edition 45, pp. 1557-1559, 2006.

Jiang et al., "Au@ZIF-8: CO Oxidation over Gold Nanoparticles Deposited to Metal-Organic Framework," J. Am. Chem. Soc., vol. 131, pp. 11302-11303, 2009.

Kubickova et al., "Hydrocarbons for diesel fuel via decarboxylation of vegetable oils," Catalysis Today 106, pp. 197-200, 2005.

Laurent and Delmon, "Study of the hydrodeoxygenation of carbonyl, carboxylic and guaiacyl groups over sulfided CoMo/y-A1203 and NiMo/y-A1203 catalysts. I. Catalytic reaction schemes," Applied Catalysis A: General 109(1), pp. 77-96, 1994.

Laurent and Delmon, "Study of the hydrodeoxygenation of carbonyl, carboxylic and guaiacyl groups over sulfided CoMo/y-A1203 and NiMo/y-A1203 catalysts. II. Catalytic reaction schemes," Applied Catalysis A: General 109(1), pp. 97-115, 1994.

(56) References Cited

OTHER PUBLICATIONS

Leclercq et al., "Transesterification of rapeseed oil in the presence of basic zeolites and related solid catalysts," J. Am. Oil Chem. Soc., 78, pp. 1161-1165, 2001.
Lee et al., "Use of Branched-Chain Esters to Reduce the Crystallization Temperature of Biodiesel," J. Am. Oil Chem. Soc., vol. 72, pp. 1155-1160, 1995.
Lee et al., "Reducing the Crystallization Temperature of Biodiesel by Winterizing Methyl Soyate," J. Am. Oil Chem. Soc., vol. 73, No. 5, pp. 631-636, 1996.
Lestari et al., "Catalytic Deoxygenation of Stearic Acid and Palmitic Acid in Semibatch Mode," Catalysis Letters 130: 48-51, 2009.
Lok et al., "Silicoaluminophosphate Molecular Sieves: Another New Class of Microporous Crystalline Inorganic Solids," J. Am. Chem. Soc., vol. 106, pp. 6092-6093, 1984.
Ma and Hanna, "Biodiesel production: a review," Bioresource Technology, vol. 70, pp. 1-15, 1999.
Maier et al., "Gas phase decarboxylation of carboxylic acids," Che. Ber., 115(2), pp. 808-812, 1982.
Maki-Arvela et al., "Catalytic Deoxygenation of Fatty Acids and Their Derivatives," Energy & Fuels, 21, pp. 31-34, 2007.
Morris et al, "Crystals as Molecules: Postsynthesis Covalent Functionalization of Zeolitic Imidazolate Frameworks," J. Am. Chem. Soc., vol. 130, pp. 12626-12627, 2008.
Murzin et al., "Deoxygenation of palmitic and stearic acid over supported Pd catalysts effect of metal dispersion," Applied Catalysis A: General, vol. 355, pp. 100-108, 2009.
Nowak et al., "Catalytic properties of niobium and gallium oxide systems suported on MCM-41 type materials," App. Catalysis A: General, vol. 325, pp. 328-335, 2008.
Phan, et al., "Synthesis, Structure, and Carbon Dioxide Capture Properties of Zeolitic Imidazolate Frameworks," Accounts of Chemical Research, vol. 43, No. 1, pp. 58-67, 2010.
Schuchardt et al., "Transesterification of vegetable oils: a review," J. Braz. Chem. Soc., vol. 9, No. 3, pp. 199-210, 1998.
Snare et al., "Heterogeneous Catalytic Deoxygenation of Stearic Acids for Production of Biodiesel," Ind. Eng. Chem. Res., vol. 45, pp. 5708-5712, 2006.
Sreeprasanth et al., "Hydrophobic, solid acid catalysts for production of biofuels and lubricants," Applied Catalysis A: General, vol. 314, pp. 148-159, 2006.
Tsuzuki et al., "cis/trans-isomerisation of triolein, trilinolein and trilinolenin induced by heat treatment," Food Chemistry, vol. 108, pp. 75-80, 2008.
Venna et al., "Structural Evolution of Zeolitic Imidazolate Framework-8," J. Am. Chem. Soc., vol. 132, pp. 18030-18033, 2010.
Venna and Carreon, "Highly Permeable Zeolite Imidazolate Framework-8 Membranes for CO2/CH4 Separation," J. Am. Chem. Soc., vol. 132, pp. 76-78, 2010.
Wang et al., "Colossal cages in zeolitic imidazolate frameworks as selective carbon dioxide reservoirs," Nature, vol. 453, pp. 207-212, 2008.
Yakovliev et al., "Development of new catalytic systems for upgraded bio-fuels production from bio-crude and biodiesel," Catalysis Today, vol. 144, pp. 362-366, 2009.
Chizallet et al., "Catalysis of Transesterification by a Nonfunctionalized Metal-Organic Framework: Acido-Basicality of the External Surfact of ZIF-8 Probed by FTIR and ab initio Calculations," J. Am. Chem. Soc. 132, pp. 12365-12377, pub. on web Aug. 2010.
PCT Notification of Transmittal of the International Search Report and the Written Opinion of the International Searching Authority, or the Declaration, Jul. 13, 2012 including the Pubwest Search History dated Jun. 20, 2012.
Adenike, et al. Production of Diesel-Like Fuel and Other Value-Added Chemicals from Pyrolysis of Animal Fat. Energy & Fuels 2005; 19 (4), 1735-1741.
Albers, et al. Poisoning and deactivation of palladium catalysts. Journal of Molecular Catalysis. 2001; vol. 173, 275-286.
Albrecht, et al. A Brief Literature Overview of Various Routes to Biorennewable Ruels from Lipids for the National Alliance for Advanced Biofuels and Bio-products (NAABB) Consortium. Pacific Northwest National Laboratory. Mar. 2011. PNNL-20279.
Alencar, et al. Pyrolysis of tropical vegetable oils. J. Agric. Food Chem., 1983, 31 (6), pp. 1268-1270.
Dandik, et al. Catalytic Conversion of Used Oil to Hydrocarbon Fuels in a Fractionating Pyrolysis Reactor. Energy & Fuels. 1998; 12 (6), 1148-1152.
Doll, et al. Comparing Biofuels Obtained from Pyrolysis, of Soybean Oil or Soapstock, with Traditional Soybean Biodiesel: Density, Kinematic Viscosity, and Surface Tensions. Energy & Fuels 2008; 22 (3), 2061-2066.
Foglia, et al. Decarbonylation Dehydration of Fatty Acids to Alkenes in the Presence of Transition State Metal Complexes. J. Am. Oil Chem. Soc. 1976, 53, 737-741.
Fu, et al. Catalytic hydrothermal deoxygenation of palmitic acid. Energy & Environmental Science 2010, Applied Catalysts A: General, 2010, vol. 3, 311-317.
Kasza, et al. Production of Bio Gas Oil from Bioparaffins over PT/SAPO-11. Chemical Engineering Transactions. 2010; 21:1225-1230.
King, et al. Hydrolysis of soybean oil. in a subcritical water flow reactor . Green Chem., 1999; 1, 261-264.
Li, et al. Catalytic Hydrothermal Conversion of Triglycerides to Non-ester Biofuels. Energy & Fuels 2010; 24 (2), 13050-1315.
Parmon, V. Catalytic Technologies for Energy-Production and Recovery in the Future. Catalysis Today, vol. 35, No. 1-2, 153-162, 1997.
Saka, et al. NEDO "High-efficiency Bioenergy Conversion Project"—R & D for Biodiesel Fuel (BDF) by Two-step Supercritical Methanol Method. Available at http://www.biomass-asia-workshop.jp/biomassws/01workshop/material/No21-Kyoto-Univ.pdf. Accessed Oct. 24, 2012.
Schwab, et al. Diesel fuel from thermal decomposition of soybean oil. J Am Oil Chem Soc. 1988;65(11):1781-1786.
Simakova, et al. Deoxygenation of Palmitic Stearic Acid over supported Pd Catalysts, Effect of Metal Dispersion. Applied Catalysts A: General, Jan. 2009, vol. 355, 100-108.
Bertram, S.H., Action of Selenium on Stearic Acid, Chem. Weekblad, 1936, 33, 457-459.

\* cited by examiner

CATALYTIC ISOMERISATION OF LINEAR OLEFINIC HYDROCARBONS

CROSS REFERENCE TO RELATED U.S. APPLICATION

This application claims priority to U.S. Provisional Application No. 61/469,384, titled "Catalytic isomerisation of linear, olefinic hydrocarbons," filed on Mar. 30, 2011.

FIELD OF INVENTION

The invention relates to catalytic isomerisation of linear olefinic hydrocarbons to branched isomers, wherein under certain conditions the branched isomers provide advantageous properties compared to their linear analogs.

BACKGROUND

Hydrocarbons are an energy source for internal combustion engines, for turbines in jet aircraft, and for other kinds of engines, as well as for other applications that require a source of fuel. For example, hydrocarbon fuels like gasoline are made up of hydrocarbons having about 4-9 carbon atoms in their molecular structure. Kerosene fuels (about 9-15 carbon atoms), jet fuels (9-15 carbon atoms), and diesel fuels (12-20 carbon atoms) are other examples. Lubricant base oils, which have a relatively higher viscosity index than the other examples, typically have 22-35 carbon atoms.

For some time, hydrocarbon fuels, in addition to other petrochemical products, have been obtained from crude petroleum oil through a series of conventional steps. Such steps include, but are not necessarily limited to, distillation followed by additional refining. Attempts are being made, however, to produce hydrocarbon fuels from alternative, renewable sources, including but not limited to feedstocks of biological origin. Moreover, because of their similar chemical properties and functional properties, some hydrocarbon fuels that are from alternative, renewable sources are compatible with and, therefore, acceptable for use with, the kinds of engines for which petroleum-derived hydrocarbon fuels are intended.

More specifically, hydrocarbon fuels, which are from alternative, renewable sources other than petroleum, include those products which are obtained from catalytic isomerisation of linear, olefinic hydrocarbons, as described and taught herein. In some cases, such products are capable of being stored and transported through existing infrastructure (e.g., storage tanks and pipelines) as with petroleum-derived hydrocarbon fuels. This improves the feasibility of using such products as replacements for petroleum-derived hydrocarbon fuels in their applications as fuels.

The words "linear" and "branched" refer to the molecular structure of a hydrocarbon's skeletal chain. In some applications relating to fuels, lubricants, and petrochemical products, the hydrocarbons are linear. In other applications, the hydrocarbons are branched. In some applications, including some in which hydrocarbons are primary constituents for gasoline, kerosene fuels, jet fuels, and diesel fuels, the use of branched hydrocarbons is advantageous over the use of their linear hydrocarbon analogs.

For example, methylhexane is the branched analog of normal heptane. Methylhexane, with an octane number of 44, has a higher octane number than normal heptane, which has an octane number of zero. Branched hydrocarbons with about 9-15 carbon atoms, e.g., when used as kerosene or jet fuel, have lower freezing points and lower pour points than their linear analogs. In certain cold temperature conditions, such properties are advantageous when compared to the properties of linear hydrocarbons having the same number of carbons. Likewise, branched hydrocarbons used in diesel fuels, which are typically 12-20 carbon atoms in length, have lower freezing points and lower pour points than their linear analogs. In the case of lubricant base oils containing 20-35 carbon atoms, branched analogs have lower freezing points and higher viscosity indices than their linear counterparts.

Besides the difference between linear branched, another consideration is whether hydrocarbons contained in fuels, lubricants, and petrochemical products are paraffinic (saturated) or olefinic (unsaturated). Under certain conditions, such as cold temperature, olefinic hydrocarbons provide various advantages over the use of paraffinic hydrocarbons containing the same number of carbon atoms, including but not limited to lower freezing points and lower pour points.

Branched olefinic hydrocarbons, e.g., of the kind which can be used as replacements for petroleum-derived hydrocarbon fuels, do not occur naturally in large supply. However, starting materials for the production of branched olefinic hydrocarbons, for example biomass raw materials, are found naturally in relatively large supply. Accordingly, such starting materials are considered to be an alternative, renewable source of hydrocarbon fuels. For example, the lipid portions of plant oils, animal fats, animal oils and algae oils are a ready source of triglycerides, which are converted to carboxylic acids through methods known to persons of ordinary skill in the art, such as hydrolysis that produces carboxylic acids and glycerine. In turn, various methods are known to persons of ordinary skill in the art for the conversion of carboxylic acids to linear olefinic hydrocarbons, where the carboxylic acid is of the formula R—COOH and R is an olefinic hydrocarbon group. These include hydrodeoxygenation, or (alternatively) decarboxylation, or (alternatively) decarbonylation. If the carboxylic acid starting materials are unsaturated, then the resulting hydrocarbon will be a linear, olefinic hydrocarbon. For example, oleic acid ($C_{17}H_{33}COOH$) is a monounsaturated fatty acid found in olive oil. The above-mentioned oxygen-removal methods convert oleic acid to heptadecene or octadecene, which are linear, olefinic hydrocarbons.

Another known method is the conversion of linear, paraffinic hydrocarbons to linear, olefinic hydrocarbons by dehydrogenation over a metal catalyst, such as platinum, palladium, or nickel, or a combination of those. Regardless of how they are produced, the isomerisation of linear, olefinic hydrocarbons to branched olefinic hydrocarbons has been performed either at high temperatures or over solid acid catalysts, such as a zeolite or silicoalumina catalyst. However, the isomerisation reactions under such conditions, and/or with the use of such catalysts, generally produce a relatively high percentage of shorter-chain, lower molecular weight hydrocarbon products due to hydrocracking. Accordingly, there is a need for a suitable catalyst and/or catalytic process for the isomerisation of branched olefinic hydrocarbons from linear, olefinic hydrocarbons. There is also a need for such a catalyst and/or catalytic process with suitable selectivity for isomerisation, as opposed to reactions that may be less desirable in certain situations, such as hydrocracking.

SUMMARY OF INVENTION

The present embodiments provide suitable catalysts and/or catalytic processes for the isomerisation reaction of linear, olefinic hydrocarbons to branched olefinic hydrocarbons, with suitable selectivity for isomerisation, as opposed to reactions that may be less desirable in certain situations, such as hydrocracking. In some embodiments, the isomerisation reaction occurs over mixed gallium-niobium oxide catalysts, and comprises the steps of contacting linear olefinic hydrocarbon reactants with the catalyst and isolating the branched olefinic hydrocarbon products through methods known to those skilled in the art.

Multiple Embodiments and Alternatives

Like their branched analogs, linear olefinic hydrocarbons do not occur naturally in abundant supply. However, various methods discussed above exist for obtaining linear olefinic hydrocarbons from sources that are found naturally in relatively large supply. The present embodiments convert linear olefinic hydrocarbons to their branched olefinic hydrocarbons through catalytic isomerisation. The approach recognizes that, regardless of which route or process as discussed in the Background is employed, linear hydrocarbons (both paraffinic and olefinic) are capable of being produced or obtained from sources that are in relatively large supply.

In some embodiments, the linear olefinic hydrocarbon starting materials and the branched products have four or more carbon atoms, and the number of carbons in the branched products equals the number of carbons in the starting materials. In some embodiments, the starting materials and products have no more than 35 carbons, and the number of carbons in the branched products is equal to the number of carbons in the starting materials. The process comprises (1) obtaining, or producing, a supply of at least one linear, olefinic hydrocarbon; (2) selecting, or preparing, a catalyst; and (3) contacting the at least one linear, olefinic hydrocarbon with the catalyst, under conditions as described herein. In some embodiments, the reaction is carried out at a temperature between 150-450° C.

Among other factors, the selectivity for branched olefinic hydrocarbon products is influenced by the number of acid sites on the catalyst, and the strength of the acid sites. Generally, if all other factors are substantially equal, then catalysts with relatively high acidity are more prone to hydrocracking than those catalysts with lower acidity.

In some embodiments, the reaction catalyst is a mixed oxide of gallium-niobium, prepared as follows. An inorganic precursor is dissolved in alcohol, for example one chosen from the group methanol, ethanol, propanol, isopropanol, butanol, isobutanol, and tertiary butanol. A structure directing agent is dissolved in an alcohol, for example ethanol or isopropanol. In some embodiments, the structure directing agent is a triblock copolymer, for example one chosen from the group cetyltrimethylammonium bromide (CTAB), Pluronic F-127, and Pluronic P-123. The precursor solution is then reacted with the triblock copolymer solution, by addition of a sufficient amount of the latter, dropwise, to the inorganic precursor solution at an appropriate temperature which, in some embodiments, is 40° C. The resulting solution is stirred for a sufficient amount of time (e.g., 30 minutes in some embodiments). The resulting homogenous gel is transferred to an autoclave and heated at about 180° C. under autogeneous pressure in a static condition for about 20 hours.

The resulting solid catalytic material is separated, washed at least once with water, and dried overnight at 100° C., then calcined in air at about 350° C. for a sufficient amount of time, for example 5-10 hours. A solid catalyst prepared in this way takes the form of spheres with a particle size distribution typically ranging from about 0.3 mm-2 mm. Generally, the nitrogen adsorption-desorption isotherms of the solid catalysts display type-IV adsorption isotherms, typical of mesoporous material. The solid catalysts prepared in this way display a range of mesophases indicative of the semi-crystalline nature of the material.

Surface area of a solid catalyst that was prepared ranged up to 366 m$^2$/g, with unimodal average pore size of about 3 nanometers (nm)-7 nm. By comparison, surface area of mesoporous niobium oxide is generally about 200 m$^2$/g. Generally, the niobium content of the mixed oxide was inversely proportional to pore size, yet proportional to the size of the spheres and surface area.

Based on X-ray diffraction pattern studies, average size of the crystallites for the mixed oxides prepared in this way was relatively small, i.e., about 3 nm-5 nm. Likewise, average size of the crystallites for niobium oxide was approximately the same. By comparison, average size of the crystallites for gallium oxide was about 14 nm. Based on high resolution transmission electron micrographs, the mixed gallium-niobium oxides displayed similar particle size (about 3 nm-4 nm) as niobium oxide. The gallium-niobium oxides as well as pure niobium oxide ($Nb_2O_5$) alike displayed broad and diffusive electron diffraction ring spacing. For the mixed oxides, the rings corresponded to "d" spacings of 0.39 nm, 0.199 nm, and 0.169 nm, respectively, which correspond to "d"-spacings of (001), (002), and (182) planes in pure niobium oxide.

According to present embodiments, linear, olefinic hydrocarbons are passed over a gallium-niobium mixed oxide catalyst in a reactor or a reaction zone according to process steps and conditions as specified herein. In some embodiments, the normal, linear olefinic hydrocarbons contain at least 4 carbon atoms. In some embodiments, the reaction is carried out at temperatures in the range of about 150°-450° C., preferably 200-400° C., and a pressure of about 1 bar-60 bar. In some embodiments, the reaction is carried out in a batch reactor. Alternatively, the reaction is carried out in a semi-batch reactor, or a continuous flow reactor. In some embodiments, the starting materials are reacted while in a liquid state, or, alternatively, in a gaseous state. At the conclusion of the reaction, the branched olefinic hydrocarbon products are separated from the effluents within the reactor.

In connection with the example described herein, gallium-niobium oxide catalysts were prepared, as were gallium oxide and niobium oxide catalysts, as summarized in Table 1 below. The catalysts were prepared by reacting solutions of gallium and niobium precursors in alcohol with Pluronic F-127. For the inorganic precursor, mole ratios of precursor:SDA:ethanol were $1:6.1\times10^{-3}:350\times10^{-3}:9$. The synthesis mole ratios of gallium to niobium prior to completing synthesis ranged from 0.2:1 to 6.6:1. Induced Coupled Plasma (i.e., ICP) is also used to determine molar composition. The ICP-determined mole ratio of gallium to nobium may differ from the synthesis mole ratio to the extent some gallium remains in solution rather than being incorporated in the catalyst. In some embodiments, the ICP-determined mole ratio of gallium to niobium is between about 0.03:1 and 2.8:1.

During synthesis, an alcoholic solution of the structure directing agent was added dropwise to the solution of gallium and niobium precursors in ethanol, at 40° C. The resultant solution was stirred for approximately 30 minutes. The resulting homogeneous gel was then transferred to a 45 ml Teflon-lined autoclave (Parr Instruments, Inc.) and heated under autogeneous pressure in a static condition in a conventional oven at 180° C. for approximately 20 hours. The white, solid catalytic material was separated by centrifuge, washed twice with water, and dried overnight at approximately 120° C., then calcined in air at 350° C. for 10 hours. Surface area of the mixed gallium-niobium oxide catalysts was determined to be within a range of about 210 m$^2$/g-366 m$^2$/g. Average pore size of the mixed oxide catalysts ranged from about 3.5 nm-6.0 nm. Average pore volume of the mixed gallium-niobium oxides ranged from about 0.23 ml/g-0.42 ml/g.

TABLE 1

Composition and physiochemical properties of prepared mesoporous Ga—Nb oxide catalysts for isomerisation of linear olefine hydrocarbons.

| Sample ID | ICP composition (Ga/Nb molar ratio) | Surface area (BET) | Average pore size (nm) | Average pore volume (cm$^3$/g) | Average particle size (μm) |
|---|---|---|---|---|---|
| Ga$_2$O$_3$ (comparable) | — | 175 | 7.3 | 0.32 | 0.3 |
| (A) GaNb$_1$ | 2.80 | 210 | 6.1 | 0.38 | 0.5 |
| (B) GaNb$_2$ | 0.84 | 366 | 4.4 | 0.42 | 0.8 |
| (C) GaNb$_3$ | 0.14 | 270 | 4.1 | 0.33 | 0.8 |
| (D) GaNb$_4$ | 0.08 | 231 | 3.7 | 0.25 | 1.0 |
| (E) GaNb$_5$ | 0.03 | 242 | 3.4 | 0.23 | 1.3 |
| Nb$_2$O$_5$ (comparable) | — | 196 | 3.2 | 0.17 | 1.8 |

EXAMPLE 1

Catalytic Isomerisation of Linear, Olefinic Hydrocarbons

Catalyst D was prepared as described above, then dried in a flow of nitrogen at 200° C. for 5 hours. The dried catalyst was loaded in a high pressure autoclave reactor (Parr Instruments, Inc.). A feedstock of normal hexadecene, a linear olefinic hydrocarbon with 16 carbon atoms, was contacted, under stirring, with the catalyst at a temperature of 250° C. and hydrogen pressure of 20 bar for 3 hours. After an additional 2 hours, the reactor was cooled to room temperature, and the catalyst was separated from the reaction products by filtration. The identity of the hydrocarbon products was determined by gas chromatography using a Hewlett Packard 4890 gas chromatograph. The hydrocarbon layer contained penta-, hexa-, hepta-, and octa-decenes. The conversion of hexadecene was 78.3%. Conversion products included branched olefinic hydrocarbons with 16 carbon atoms (63.3%) as well as branched olefinic hydrocarbons with less than 16 carbon atoms (27.0%).

The iodine number of the hexadecene feedstock was 109.1. The iodine number of the conversion products as a whole was 145.8. This indicates that the number of double bonds in some of the conversion products exceeded the number of double bonds in the feedstock, indicating that some diolefins are also present in the products. Accordingly, besides the conversion of linear hexadecene to branched iso-decenes, this mixed gallium-niobium oxide catalyst also dehydrogenated some of the monounsaturated olefins to diolefins.

The above example is non-limiting and merely characteristic of multiple alternative embodiments taught and described herein. Further, it is to be understood that the embodiments described herein are not limited in their application to the details of the teachings, descriptions, and examples set forth herein. Rather, it will be understood that a process for catalytic isomerisation of linear, olefinic hydrocarbons, as taught and described according to multiple embodiments disclosed herein, is capable of other embodiments and of being practiced or of being carried out in various ways by persons having ordinary skill in the art.

Also, it is to be understood that the phraseology and terminology used herein is for the purpose of description and should not be regarded as limiting. The use herein of "including," "comprising," "e.g.," "such as," "for example," "containing," or "having" and variations of these words and phrases is meant in a non-limiting way to encompass the items listed thereafter, and equivalents of those, as well as additional items.

Accordingly, the foregoing descriptions are meant to illustrate a number of embodiments and alternatives, rather than to serve as limits on the scope of what has been disclosed herein. The descriptions herein are not intended to be exhaustive, nor are they meant to limit the understanding of the embodiments to the precise forms disclosed

We claim:

1. A process for catalytic isomerisation of linear, olefinic hydrocarbons, comprising the steps of:
    contacting linear olefinic hydrocarbon reactants with a catalyst; and
    isolating branched olefinic hydrocarbon products,
    wherein the catalyst is a solid gallium-niobium mixed oxide catalyst having a synthesis mole ratio of gallium to niobium between about 0.2:1 and 6.6:1 and a surface area of at least 210 m$^2$/g.

2. The process of claim 1, wherein the surface area of the catalyst is between about 300 m$^2$/g and 366 m$^2$/g.

3. The process of claim 1, wherein the ICP-determined mole ratio of gallium to niobium is between about 0.03:1 and 2.8:1.

4. The process of claim 1, carried out at a temperature between about 150° C. and about 450° C.

5. The process of claim 4, carried out at a temperature no greater than about 400° C.

6. The process of claim 1, wherein each linear olefinic hydrocarbon reactant has no more than 35 carbons.

7. The process of claim 6, wherein each linear hydrocarbon reactant has between 4 and 19 carbons.

8. The process of claim 1, wherein the catalyst is prepared by adding a solution of at least one structure directing agent in alcohol to a solution of gallium and niobium in alcohol under conditions and for a duration sufficient to react a sufficient amount of the reactants to form a mixed gallium-niobium oxide catalyst having a synthesis mole ratio of gallium to niobium between about 0.2:1 and 6.6:1.

* * * * *